United States Patent [19]

Sobol

[11] 4,049,200
[45] Sept. 20, 1977

[54] NEBULIZER

[76] Inventor: Jacob M. Sobol, 62 Tet Zayin, Zefat, Israel

[21] Appl. No.: 674,044

[22] Filed: Apr. 5, 1976

[51] Int. Cl.² .............................................. B05B 7/26
[52] U.S. Cl. .................................. 239/338; 239/343; 239/432
[58] Field of Search ............... 239/338, 343, 432, 542, 239/370, 121, 305; 128/194

[56] References Cited

U.S. PATENT DOCUMENTS

| | | | |
|---|---|---|---|
| 2,069,455 | 2/1937 | Massa | 239/370 X |
| 2,495,587 | 1/1950 | Magowan | 239/305 X |
| 2,807,504 | 9/1957 | Bloxsom | 239/338 |
| 3,591,090 | 7/1971 | Carden | 239/305 |
| 3,799,441 | 3/1974 | Delmer | 239/542 X |
| 3,867,092 | 2/1975 | Sage et al. | 239/432 X |

*Primary Examiner*—Evon C. Blunk
*Assistant Examiner*—Michael Mar
*Attorney, Agent, or Firm*—Gust, Irish, Jeffers & Rickert

[57] ABSTRACT

A nebulizer having an elongate housing supporting an air nozzle in aspirating relation to a liquid nozzle in an interior chamber of the housing to vaporize the liquid. Baffle discs each having a chordal section removed therefrom are placed in parallel spaced relation in the chamber substantially transverse to the direction of vapor flow in the chamber. The openings formed by the chordal sections of adjacent discs are non-aligned causing the vapor flow to follow a tortuous path, and impinge upon a baffle surface, collapsing larger liquid droplets in the vapor which collect in the chamber. A liquid flow control valve in one position connects the liquid nozzle to the accumulated liquid in the chamber, or to an external reservoir, and in a second position, to an exterior source of liquid.

7 Claims, 6 Drawing Figures

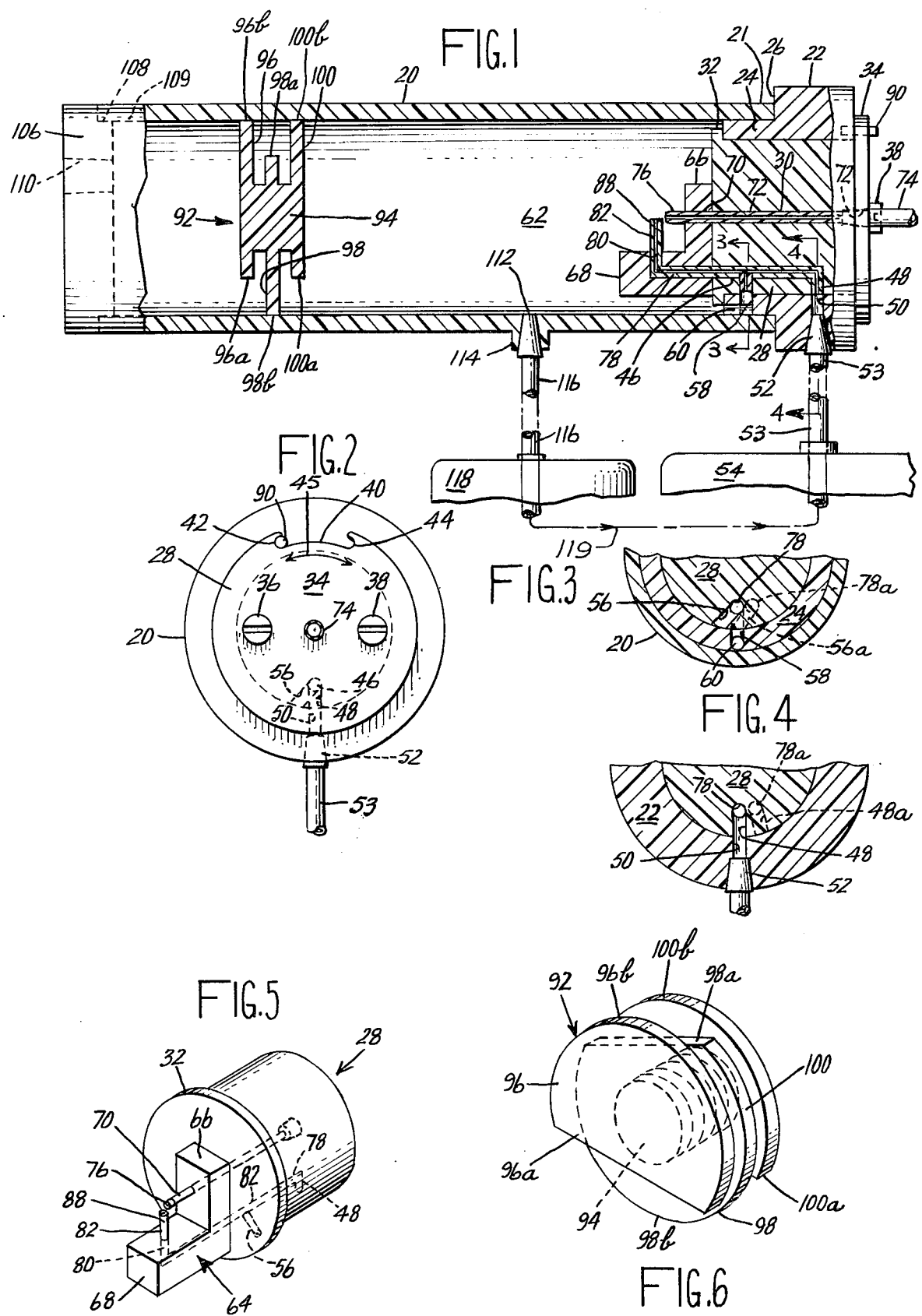

NEBULIZER

BACKGROUND OF THE INVENTION

1. Field of the Invention

This invention is in the field of atomizers or nebulizers for producing a vapor of controlled composition that is useful as a medicant and diagnostic inhalant, in humidification, as well as in other uses.

2. Description of the Prior Art

Atomizers or nebulizers for producing a fine mist or vapor are well known to the art and are well documented over the years by issued patents. The art has been striving to provide a simple yet effective nebulizer and various combinations of atomizing devices and baffles have been used to produce a uniform mist or vapor. However, the flexibility of operation is limited in the prior art devices and the baffle efficiency has not been entirely satisfactory.

SUMMARY OF THE INVENTION

An elongate, tubular housing supports an air nozzle at one end to conduct air flow under pressure longitudinally of a chamber interior of the housing. A liquid nozzle is supported in aspirating relation to the air nozzle in the chamber and is in communication with a liquid supply, the liquid being aspirated and vaporized by air flow through the air nozzle. A liquid flow control member, or valve, in one position connects the liquid nozzle to accumulated liquid in the lower portion of the chamber, or to an external reservoir, and in a second position connects the liquid nozzle to an exterior source of liquid thus providing a small, self-contained liquid supply or a connection to a substantially larger supply as desired. The control member comprises a core element rotatably mounted in one housing end. Supported centrally on the core is the air nozzle and supported radially on the core is the liquid nozzle. Passages are formed in the core to connect the air nozzle to an air supply regardless of the rotative core position and to connect the liquid nozzle to the lower chamber portion or external liquid supply depending on the rotative core position.

At the housing end opposite and distal from the core is the nebulizer output. Interposed between the output and the core is a baffle assembly having a plurality of parallel spaced transverse discs of a diameter equal to the chamber diameter. Each disc has a chordal segment removed to form a passage for the vapor. The passages of adjacent discs are nonaligned so that the vapor flow through the baffle is in a tortuous path against and along a plurality disc surfaces. It has been found that this baffle assembly is highly efficient and collapses vapor droplets greater than about ½ micron in diameter producing a mist that will not cohere or adhere, will go through bronchioles, and will not condense on a polished surface at ambient temperatures.

It is therefore an object of this invention to provide an improved nebulizer for providing a uniformly fine vapor.

Another object is to provide an improved nebulizer of the foregoing object wherein the liquid to be nebulized may be self-contained in the nebulizer or in an exterior liquid container.

The above-mentioned and other features and objects of this invention and the manner of attaining them will become more apparent and the invention itself will be best understood by reference to the following description of an embodiment of the invention taken in conjunction with the accompanying drawings.

BRIEF DESCRIPTION OF THE DRAWINGS

FIG. 1 is a partially sectioned view of a preferred embodiment of this invention;

FIG. 2 is an end view of the embodiment of FIG. 1 as viewed from the right;

FIG. 3 is a section taken at 3—3 of FIG. 1;

FIG. 4 is a section taken at 4—4 of FIG. 1;

FIG. 5 is a view in perspective of the nozzle drum and support of FIG. 1; and FIG. 6 is a view in perspective of the baffle assembly used in the embodiment of FIG. 1.

DESCRIPTION OF A PREFERRED EMBODIMENT

Referring to FIG. 1, elongated tubular housing 20 supports at one end 21 a mounting ring 22 having annular sleeve 24 extending therefrom and forming shoulder 26 which is insertable in end 21 of housing 20 in a tight frictional fit, end 21 of housing 20 abutting shoulder 26. Rotatably mounted in ring 22 is nozzle drum 28 having central bore 30 and end flange 32. Drum plate 34 is secured to drum 28 by threaded fasteners 36, 38 threadedly received in drum 28. Flange 32 and plate 34 serve to axially locate drum 28 on ring 22. Each of bolts 36, 38 have protruding heads which are used, as will become apparent, as finger access surfaces to rotate drum 28 in ring 22.

Plate 34 has formed in the periphery thereof arcuate slot 40 having slot ends 42, 44. As will become apparent, the length of slot 40 determines the rotative travel limits of drum 28 in ring 22, as shown by arrow 45.

Also formed in drum 28 is off-center axially parallel bore 46 which has at one end thereof radially extending passage 48 which is registrable with radially extending passage 50 in ring 22. Passage 50 has a smooth, tapered opening adapted to receive commercially available standard hypodermic syringe tip 52 of flexible plastic tube 53 connected to liquid container 54 which may be a soft intravenous bottle or pack. Container 54 may contain a liquid medicant, a radiopaque substance or other liquid which is to be nebulized for use in medical, radiography, industrial or other uses. Tube 53 may be of any desired length to facilitate movement of housing 20 independently of container 54.

Also formed in drum 28 and in fluid communication with passage 46 is chordal passage 56 (FIG. 3) which extends between passage 46 and the exterior of drum 28. Passage 56 is registrable with radially extending passage 58 (FIG. 3) in sleeve 24 and axially parallel passage 60 in sleeve 24 which communicates with the lower portion of chamber 62 in housing 20.

Attached to the end of drum 28, as by an adhesive, is L-shaped support 64 (FIG. 5) having leg 66 and base 68. Formed in leg 66 is axial passage 70 which is aligned with passage 30 in drum 28 and supports tube 72 which provides fluid communication between a pneumatic pressure source, not shown, through a flexible tube 74. A smooth, tapered opening 73 receives hypodermic syringe tip 38 on tube 74. Tube 72 has a tapered end 76 protruding into chamber 62 which forms an air nozzle. Axially parallel passage 78 is formed in base 68 and registers with passage 46 in drum 28. Transverse passage 80 in base 68 extends from the inner end of passage 78 inwardly toward nozzle 76. Tube 82 is supported in passages 48, 78, and 80 and has an opening therein approximately midway thereof which communicates with passage 56. One end of tube 82 communicates with tip 52. The other end 88 of tube 82 is closely adjacent but not touching the horizontal diameter of nozzle 76 whereby air flow through nozzle 76 of sufficient velocity will cause aspiration of liquid through tube 82 and nozzle 88. Air flow through nozzle 76 may be controlled for optimum results in the various applications of this invention.

Pin 90 is fixedly supported in ring 22 and extends in an axially parallel direction from the end thereof in slot 40. Pin 90 in cooperation with slot ends 42 and 44 determines the rotative travel limits of drum 28. In the angular rotative position shown in FIG. 2, slot end 42 is abutting pin 90, and passages 48 and 50 are aligned (FIG. 4), and tube 82 is in communication with tip 52 of tube 53. The communication between tube 82 and tubular passage 60 is interrupted since passage 56 is unaligned with passage 58 (FIG. 3).

Rotating drum 28 counterclockwise until slot end 44 abuts pin 90, moves passage 48 to position **48*a* (FIG. 4) and the communication between tube 82 and spout 52 is interrupted since passages 48 and 50 are no longer aligned. However, in this rotative position passage 56 is in position 56*a* (FIG. 3) and communication between tube 82 and tubular passage 60 is established since passage 56 is now aligned with passage 60. The purpose of switching communication from passage 60 and spout 52** will become apparent as this description proceeds.

Located in an intermediate longitudinal position in housing 20 is baffle assembly 92. Baffle core 94 of assembly 92 supports three baffle discs 96, 98, and 100. Each disc has a chordal section removed therefrom along chordal lines **96*a*, 98*a* and 100*a*, (FIG. 6) to from disc openings. Chordal lines on adjacent discs, such as between discs 96 and 98 are in an angular position such that the angle between the disc radii which are perpendicular to chords 96*a* and 98*a* are preferably slightly less than 180°. When projected on a parallel plane, chordal lines 96*a* and 100*a* overlie. In this manner, there are no overlapping disc openings and chordal lines of adjacent discs, when projected on a common plane, do not intersect in the disc area. By having the removed chordal sections so aligned, it is seen that any fluid passing axially through the interior of housing 20 is caused to impinge upon disc surfaces as well as the inner walls of housing 20 thereby collapsing any droplets in the fluid stream which are greater than about one-half micron in diameter. Substantially all of the droplets are collapsed on disc 100 and the exposed portion of disc 98, the chamber adjacent disc 96** remaining dry.

By having three discs 96 to 100, disc circumferences **96*b* and 100*b* are in spaced contact with one side of housing 20 and circumference 98*b* is in contact with an opposite side of housing 20 to provide stabilized disc support. Preferably, the baffle is placed in housing 20 so that chords 96*a* to 100*a* are at an angle with the horizontal transverse axis of housing 20.**

A cap 106 has a boss 108 which is insertable in, and has a friction fit with the inside end 109 of housing 20. Eccentric outlet opening 110 is formed in cap 106 and is non-aligned with the disc opening formed by chordal segment **96*a* to provide a final baffle stage for the nebulized fluid. The baffling thus provided will cause a condensate liquid accumulation in the lower portion of the chamber 62 in housing 20. A drain opening 112 has a smooth, tapered opening for receiving syringe tip 114 on tube 116 and is connected to reservoir 118. Alternatively, a plug may be inserted to capture and accumulate the condensate in the housing interior chamber 62. If accumulated, the condensate will flow into passage 60. If drum 28 is rotated to its counterclockwise position, a flow of air through pipe 74 and nozzle 76 will aspirate the collected liquid through nozzle 88 from reservoir 118. Drum 28 may be rotated in a clockwise direction so that nozzle 88 is in fluid communication with the contents of liquid container 54** for aspiration therefrom.

The nebulizer shown in FIG. 1 may also be used as a compact portable unit by removing liquid container 54, rotating drum 28 in its counterclockwise position so that passage 56 is in communication with passage 60, and by filling chamber 62 through port 112 to the desired level with the liquid to be nebulized and then inserting a plug in port 112. When used in this mode, the liquid level must not interfere with the aspiration of the liquid from nozzle 88 and the contact between disc circumference 102 and the inner surface of housing 20 should be substantially liquid-tight.

Importantly, the source of aspirated liquid, whether in container 54 or reservoir 118, is below the aspirating area of tube 76 and 88 to prevent flooding and improper aspiration. The aspirated fluid is drawn up against gravity in the proper amount when the liquid is so positioned. The condensate which is collected in reservoir 118 may be reused for humidifying and the like but should not be reused when the nebulizer is vaporizing a sterilized medicant from an intravenous sack or the like. When the liquid in reservoir 118 is to be reused, passage 119 is established, otherwise, passage 119 is effectively removed, as it would be when a separate container 54 is used. Also, oxygen may be used as the aspirating fluid connected to the tube 74 and emitted from nozzle 76. Further, the nebulizer may be chemically cleaned and sterilized by merely placing the desired cleaning liquid in reservoir 118 and container 54 and aspirating in both positions of core 28. Additionally, various sized nebulizers may be used; smaller units may be desired for use as inhalants and medicants and other medical uses while larger units may be used for vaporizers or humidifiers or other large volume continuous uses.

While there have been described above the principles of this invention in connection with specific apparatus, it is to be clearly understood that this description is made only by way of example and not as a limitation to the scope of the invention.

What is claimed is:

1. Nebulizer apparatus comprising;

an elongate housing having a chamber therein and supporting a pneumatic nozzle in aspirating relation to a liquid nozzle in said chamber;

a liquid inlet formed in said housing in fluid communication with said liquid nozzle;

a pneumatic inlet formed in said housing in fluid communication with said pneumatic nozzle;

a liquid passage between said chamber and said liquid nozzle; and flow control means for selectively connecting said liquid nozzle to one of said liquid inlet and liquid passage and comprising;

a drum rotatably mounted at one end of said housing;

said pneumatic inlet comprising a first axial passage;

said drum having an eccentric axial passage parallel with said first axial passage and connected to a first transverse passage terminating in said liquid nozzle;

said liquid inlet comprising a second transverse passage in fluid communication with said eccentric passage; and said liquid passage comprising a third transverse passage in fluid communication with said eccentric passage and angularly displaced from said second transverse passage.

2. A nebulizer according to claim 1 including:

a stop element fixed to said housing;

said drum having means registerable with said element and cooperating therewith for defining first and second rotational limits of said drum; said drum at said first limit connecting said liquid inlet to said liquid nozzle and at said second limit connecting said liquid passage to said liquid nozzle.

3. A nebulizer according to claim 2 wherein said drum has a coaxial passage therein in fluid communication with said first axial passage and said pneumatic nozzle.

4. A nebulizer according to claim 3 wherein said housing has a drain opening having a removable closure therein.

5. A nebulizer according to claim 6 including means for connecting a liquid container to said housing in fluid communication with said liquid inlet.

6. A nebulizer according to claim 5 wherein said housing has an end cap distal from said drum snugly mounted in vapor sealing relation to said distal end; said end cap having an eccentric vapor outlet to form a final baffle stage.

7. A nebulizer according to claim 6 further comprising:

a plurality of planar baffle members mounted in spaced relation in said housing; each member having a surface portion removed therefrom to form an opening; the openings of two adjacent members having non-overlapping portions whereby fluid flowing through one opening will impinge on the surface of the adjacent member and change fluid direction collapsing liquid droplets on said baffle surface.

* * * * *